United States Patent
Sawamoto et al.

(10) Patent No.: US 10,539,685 B2
(45) Date of Patent: Jan. 21, 2020

(54) SCINTILLATOR

(71) Applicant: Konica Minolta, Inc., Chiyoda-ku, Tokyo (JP)

(72) Inventors: Naoyuki Sawamoto, Hachioji (JP); Takehiko Shoji, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 16/034,925

(22) Filed: Jul. 13, 2018

(65) Prior Publication Data

US 2019/0025442 A1    Jan. 24, 2019

(30) Foreign Application Priority Data

Jul. 24, 2017   (JP) ................. 2017-142631

(51) Int. Cl.
   *G01T 1/20*     (2006.01)
   *A61B 6/00*     (2006.01)

(52) U.S. Cl.
   CPC ............ *G01T 1/2002* (2013.01); *A61B 6/484* (2013.01); *G01T 1/2012* (2013.01); *G01T 1/2018* (2013.01)

(58) Field of Classification Search
   CPC ... G01T 1/2002; G01T 1/2012; G01T 1/2018; A61B 6/484
   USPC ............... 250/336.1, 370.01, 370.08, 370.11
   See application file for complete search history.

(56) References Cited

U.S. PATENT DOCUMENTS

| | | | |
|---|---|---|---|
| 4,571,496 A | 2/1986 | Arakawa et al. | |
| 5,812,629 A * | 9/1998 | Clauser | A61B 6/032 378/37 |
| 8,525,120 B2 * | 9/2013 | Iwamoto | G01T 1/2002 250/367 |
| 2004/0262536 A1 | 12/2004 | Van den Bergh et al. | |
| 2006/0033030 A1 * | 2/2006 | Ito | G01T 1/2018 250/370.11 |
| 2006/0054830 A1 * | 3/2006 | Oyaizu | C09K 11/7767 250/370.11 |
| 2008/0290285 A1 * | 11/2008 | Wakamatsu | C09K 11/616 250/370.11 |

(Continued)

FOREIGN PATENT DOCUMENTS

| | | |
|---|---|---|
| EP | 0123025 A2 | 10/1984 |
| EP | 1550885 A1 | 7/2005 |

(Continued)

OTHER PUBLICATIONS

European Patent Application No. 18184376.4; Extended Search Report; dated Sep. 27, 2018; 10 pages.

(Continued)

*Primary Examiner* — David P Porta
*Assistant Examiner* — Blake C Riddick

(57) ABSTRACT

A scintillator panel includes at least one light emitting layer and at least one non-light emitting layer laminated, wherein the light emitting layer contains phosphor particles, and when the thickness of the light emitting layer is represented by A, a relationship among a cumulative 50% particle diameter $D_{50}$ of the phosphor particles based on volume average, a cumulative 90% particle diameter $D_{90}$ of the phosphor particles based on volume average, and the thickness A satisfies, $D_{50} < A$ and $D_{90} < 2A$.

10 Claims, 4 Drawing Sheets

(56) References Cited

U.S. PATENT DOCUMENTS

| | | | | |
|---|---|---|---|---|
| 2011/0215250 A1* | 9/2011 | Ohta | ............................ | G01T 1/24 250/370.08 |
| 2013/0082184 A1* | 4/2013 | Nakatsugawa | ......... | A61B 6/4208 250/366 |
| 2013/0119260 A1* | 5/2013 | Nakatsugawa | ......... | A61B 6/4208 250/366 |
| 2014/0014846 A1* | 1/2014 | Kaneko | ....................... | G01T 1/20 250/369 |
| 2014/0093041 A1* | 4/2014 | Takei | ....................... | G01T 1/2002 378/62 |
| 2014/0239196 A1* | 8/2014 | Shoji | ......................... | G01T 1/202 250/488.1 |
| 2014/0286477 A1* | 9/2014 | Ishii | .......................... | G01N 23/04 378/62 |
| 2014/0353508 A1* | 12/2014 | Nagata | ....................... | G21K 4/00 250/361 R |
| 2015/0010130 A1 | 1/2015 | Nakatsugawa et al. | | |
| 2015/0301198 A1* | 10/2015 | Jagannathan | ......... | C09K 11/7771 250/361 R |
| 2015/0309190 A1* | 10/2015 | Kinoshita | ............... | G01T 1/2018 250/486.1 |
| 2016/0282480 A1* | 9/2016 | Yamamoto | ............... | G21K 4/00 |
| 2017/0192105 A1* | 7/2017 | Hamano | .................. | G21K 4/00 |
| 2017/0363753 A1* | 12/2017 | Arimoto | .................. | G21K 4/00 |
| 2018/0284298 A1* | 10/2018 | Arimoto | .................. | G01T 1/20 |

FOREIGN PATENT DOCUMENTS

| | | |
|---|---|---|
| EP | 3151247 A1 | 4/2017 |
| EP | 3261092 A1 | 12/2017 |
| JP | H11023798 | 1/1999 |
| JP | 2004-204053 A | 7/2004 |
| JP | A2012108158 | 6/2012 |
| JP | A2016003928 | 1/2016 |
| JP | A2016186455 | 10/2016 |
| JP | A2016217875 | 12/2016 |
| WO | WO2014080941 | 11/2013 |
| WO | WO 2014/080941 A1 | 5/2014 |

OTHER PUBLICATIONS

King et al, Flexible radioluminescence imaging for FDG-guided surgery, Med. Phys. 43(10) pp. 5298-5306 (Oct. 2016).

Rutishauser et al, Structured scintillator for hard x-ray grating interferometry, Appl. Phys. Lett. 98, 171107 (2011).

* cited by examiner

SCINTILLATOR

The entire disclosure of Japanese patent Application No. 2017-142631, filed on Jul. 24, 2017, is incorporated herein by reference in its entirety.

BACKGROUND

Technological Field

The present invention relates to a novel scintillator and a Talbot-Lau imaging device using the scintillator.

Description of the Related Art

Conventionally, a radiation image such as an X-ray image has been widely used for diagnosis of a disease at a medical site. Here, in recent years, a digital radiation image detection device typified by a computed radiography (CR), a flat panel type radiation detector (FPD), or the like has appeared. Among the digital techniques concerning an X-ray image, various studies on FPD have been performed in recent years. Here, FPD uses a scintillator panel having a phosphor (scintillator) layer formed of an X-ray phosphor having a characteristic of converting an emitted X-ray into visible light to emit light in order to convert an X-ray into visible light, and converts a visible light image generated front the scintillator panel into an electric signal using, for example, a thin film transistor (TFT).

A wavelength conversion layer includes a phosphor that converts a radiation into visible light. Particles such as GOS ($Gd_2O_2S$:Tb) (hereinafter referred to as phosphor particles) and columnar crystals such as CsI:T1 are used as this phosphor. However, a wavelength conversion layer having a particle structure is more easily manufactured and is more inexpensive than a wavelength conversion layer having a columnar crystal structure, and therefore has been used widely.

Recently, a method for observing a lesion by directly attaching a sheet-like scintillator to a patient's body surface or by attaching the sheet-like scintillator to a tissue collected by surgical excision or the like (flexible radioluminescence imaging for FDG-guided surgery Medical Physics 43, 5298 (2016)) is less invasiveness, and can perform a simple and rapid pathological diagnosis, and therefore has been highly expected. For this purpose, it has been desired to thin both a scintillator layer and a support layer.

In addition, as described in JP 2016-217875 A, an attempt has been made to extract energy information by combining many scintillator layers having different emission wavelengths, causing a higher energy X-ray to reach a deeper part of a scintillator, and changing an emission color. For example, this configuration brings about an advantage that an energy discrimination image can be constructed even with one shot although the energy discrimination image is conventionally constructed with two shots by changing a tube voltage when bone including cartilage, an ash component, or the like is measured.

In addition, as a scintillator using phosphor particles, a scintillator to which a Talbot system is applied has been highly expected.

At present, in X-ray image diagnosis, an absorption image obtained by converting attenuation of an X-ray after the X-ray passes through an object into an image is used. Meanwhile, an X-ray is one of electromagnetic waves, and therefore attention is paid to this wave nature. An attempt to convert a change in phase after an X-ray passes through an object into an image has been made recently. These are called absorption contrast and phase contrast, respectively. An imaging technique using this phase contrast has higher sensitivity to a light element than conventional absorption contrast, and therefore is considered to have high sensitivity to human soft tissues containing a large amount of light element. X-ray image diagnosis (Talbot system) using an X-ray Talbot-Lau interferometer, capable of acquiring a phase contrast image using an X-ray source conventionally used at a medical site, has been expected.

In the Talbot-Lau interferometer, as illustrated in FIG. 6, a G0 grating, a G1 grating, and a G2 grating are disposed between a medical X-ray tube and FPD, and refraction of an X-ray due to a subject is visualized as moire fringes. An X-ray is emitted in a longitudinal direction from an X-ray source disposed in an upper part and reaches an image detector through G0, a subject, G1, and G2.

A slit scintillator that imparts a grating function to a scintillator and makes the scintillator emit light in a form of a slit attracts attention. For example, Applied Physics Letter 98, 171107 (2011) "Structured scintillator for x-ray grating interferometry" (Paul Scherrer institute (PSI)) discloses a grating-shaped scintillator in which phosphor (CsI) particles are filled in a groove of a grating manufactured by etching a silicon wafer.

In addition, as a partitioned scintillator having a scintillator layer filled in a cell partitioned by a partition wall, WO 2014/080941 has proposed that by constituting a partition wall with a material containing a low melting point glass as a main component, constituting the scintillator layer with a phosphor and a binder resin, and filling the binder resin contained in the scintillator layer in the vicinity of the phosphor, scattering of light due to a surface of the phosphor can be suppressed and light scattering due to a surface of the partition wall is also suppressed.

Furthermore, as a new scintillator having a grating shape, a scintillator having a slit structure constituted by a laminate of a light emitting layer containing phosphor particles and a non-light emitting layer, configured such that an emitted X-ray emits light in the light emitting layer, the X-ray passes through the non-light emitting layer, and emitted light is detected by a sensor, has been highly expected.

As a patent document describing a particle size distribution of phosphor particles, JP 2016-3928 A discloses that, in a radiation detector including a phosphor layer and an inorganic fine particle layer that has absorbed a solvent component of a phosphor layer paste, $D1 \leq D2$ is satisfied when a particle size distribution median value of the phosphor particles in the phosphor layer is represented by D1 and a particle size distribution median value of the inorganic particles in the inorganic particle layer is represented by D2, and further discloses that $S1 \geq S2$ is satisfied when a particle size distribution width slog value of the phosphor particles in the phosphor layer is represented by S1 and a particle size distribution width slog value of the inorganic particles in the inorganic particle layer is represented by S2.

JP 2012-108158 A discloses that, in a radiation image detector that detects visible light converted by a wavelength conversion layer and converts the visible light into an image signal representing a radiation image, for improving light exchange efficiency, the wavelength conversion layer has a phosphor layer in which a first phosphor having a first average particle diameter and a second phosphor having a second average particle diameter larger than the first average particle diameter are mixed. JP 2012-108158 A discloses that the first average particle diameter is 1 μm or more and less than 5 µm and the second average particle diameter is 5 µm or more and 12 µm or less.

JP 11-23798 A discloses a radiation intensifying screen including a support and a first phosphor layer disposed on the support and including first phosphor particles having an average particle diameter D1 and having a range coefficient k representing a particle size distribution in a range of 1.3 to 1.8.

Furthermore, the present applicant has proposed a scintillator panel having a scintillator layer containing at least two kinds of scintillator particles having different average particle diameters in JP 2016-186455 A.

Attempts have been made to use phosphor particles for many uses in this way. However, irregularities on a surface of a light emitting layer (scintillator layer) cannot be reduced, and it is insufficient to secure a high modulation transfer function (MTF) by a method only using a phosphor having different particle size distributions.

In addition, in a case where the thickness of a light emitting layer itself is reduced, an influence of the particle diameters of phosphor particles becomes stronger, and some particles have diameters exceeding the thickness of the light emitting layer. As in Flexible radioluminescence imaging for FDG-guided surgery/Medical Physics 43, 5298 (2016), there is a usage example in which a light emitting layer is thin. However, as the light emitting layer becomes thinner, the particle diameter distribution of phosphor particles has a larger influence on surface irregularities, and there is concern that brightness and sharpness may be affected.

In addition, as the thickness of the light emitting layer becomes thinner, it becomes necessary to use phosphor particles having smaller particle diameters. Furthermore, the brightness becomes lower due to the thinness. Therefore, it is difficult to obtain sufficient brightness.

SUMMARY

Under such a situation, the present inventors made intensive studies to solve the above problems. As a result, the present inventors have found that by using scintillator particles having an appropriate particle size distribution with respect to the thickness of a light emitting layer, such coarse particles to distort the structure can be reduced appropriately, and therefore an ultrathin film and multilayer scintillator with improved sharpness and high accuracy can be obtained, and have completed the present invention.

To achieve at least one of the abovementioned objects, according to an aspect of the present invention, a scintillator panel reflecting one aspect of the present invention comprises at least one light emitting layer and at least one non-light emitting layer laminated, wherein the light emitting layer contains phosphor particles, and when the thickness of the light emitting layer is represented by A, a relationship among a cumulative 50% particle diameter $D_{50}$ of the phosphor particles based on volume average, a cumulative 90% particle diameter $D_{eo}$ of the phosphor particles based on volume average, and the thickness A satisfies, $D_{50} < A$ and $D_{90} < 2A$.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, a scintillator panel according to one or more embodiments of the present invention will be described with reference to the drawings. However, the scope of the invention is not limited to the disclosed embodiments.

The scintillator panel according to an embodiment of the present invention includes at least one light emitting layer and at least one non-light emitting layer laminated. The light emitting layer contains phosphor particles. When the thickness of the light emitting layer is represented by A, a relationship among a cumulative 50% particle diameter $D_{50}$ of the phosphor particles based on volume average, a cumulative 90% particle diameter $D_{90}$ of the phosphor particles based on volume average, and the thickness A satisfies, $D_{50} < A$ and $D_{90} < 2A$.

The cumulative 50% particle diameter $D_{50}$ and the cumulative 90% particle diameter $D_{90}$ can be measured by a known measurement method and can be measured using, for example, a laser scattering/diffraction method.

For example, a particle diameter can be measured using Microtrac MT 3300 II (Microtrac Bel Corporation) by dispersing phosphor particles in ethanol.

The phosphor particles have a particle diameter distribution, and some particles have diameters exceeding the thickness of the light emitting layer. This distorts the structure and lowers MTF. In general, if the thickness is thinner and a particle diameter used is smaller, brightness and sharpness are lowered. However, by satisfying a specific relational formula as in the present invention, it is possible to largely improve brightness and sharpness without presence of coarse particles to distort the structure.

Figure 4:
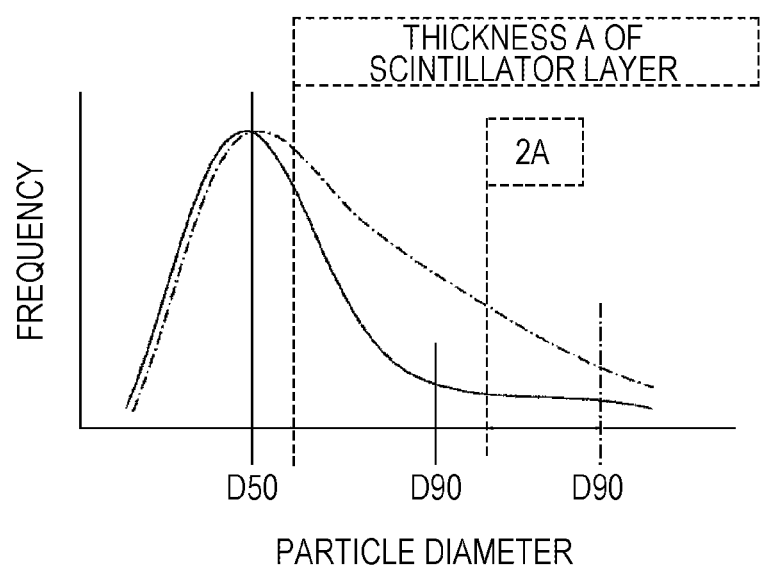
FIG. 4 is a conceptual diagram of a particle diameter distribution in which the vertical axis indicates frequency.

$D_{90}$ becomes smaller as the number of coarse particles is reduced. FIG. 4 illustrates a relationship between the cumulative 50% particle diameter $D_{50}$ and the cumulative 90% particle diameter $D_{90}$. In FIG. 4, the vertical axis indicates frequency. A sample with a small indicates that the peak of the frequency distribution is sharp. If $D_{90} < 2A$ is satisfied, the number of coarse particles affecting an optical layer is small, and it is possible to largely improve brightness and sharpness.

A relationship between $D_{50}$ and the thickness A of the light emitting layer preferably further satisfies $0.01 < (D_{50}/A) < 1$.

The cumulative 50% particle diameter $D_{50}$ and the cumulative 90% particle diameter $D_{90}$ can be adjusted by a known method such as pulverization or classification although depending on a manufacturing method. $D_{50}$ and $D_{90}$ are appropriately selected according to the thickness of an intended light emitting layer.

The thickness A of the light emitting layer is preferably 30 nm or less, and more preferably 0.15 to 15 µm. The thickness of the non-optical layer is 30 µm or less, and preferably in a range of 0.15 to 15 µm.

The average particle diameter of the phosphor particles is not particularly limited as long as the relationship with the thickness A satisfies the above formula, but is preferably 100% or less, and more preferably 90% or less with respect to the thickness A of the light emitting layer. If the average particle diameter of the phosphor particles exceeds the above range, disorder of a pitch lowers brightness and sharpness.

Figure 1:
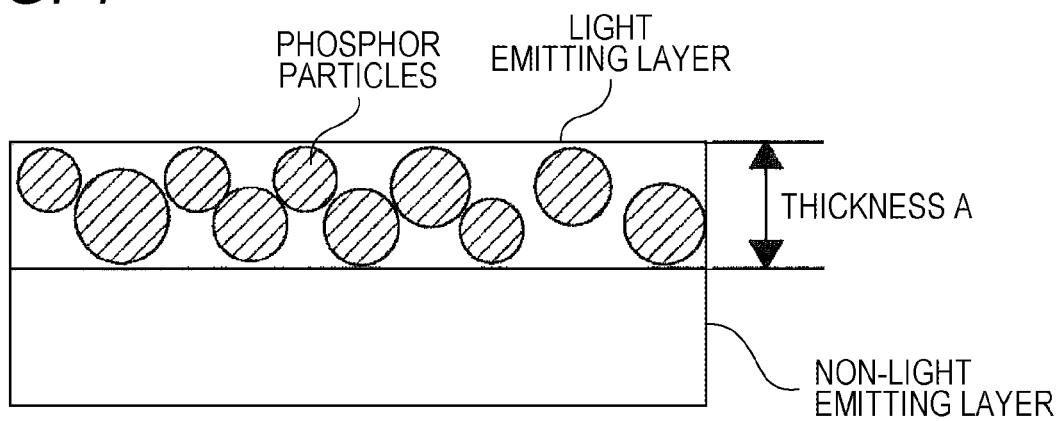
FIG. 1 is a schematic view of a scintillator panel according to one embodiment of the present invention.
Figure 2:
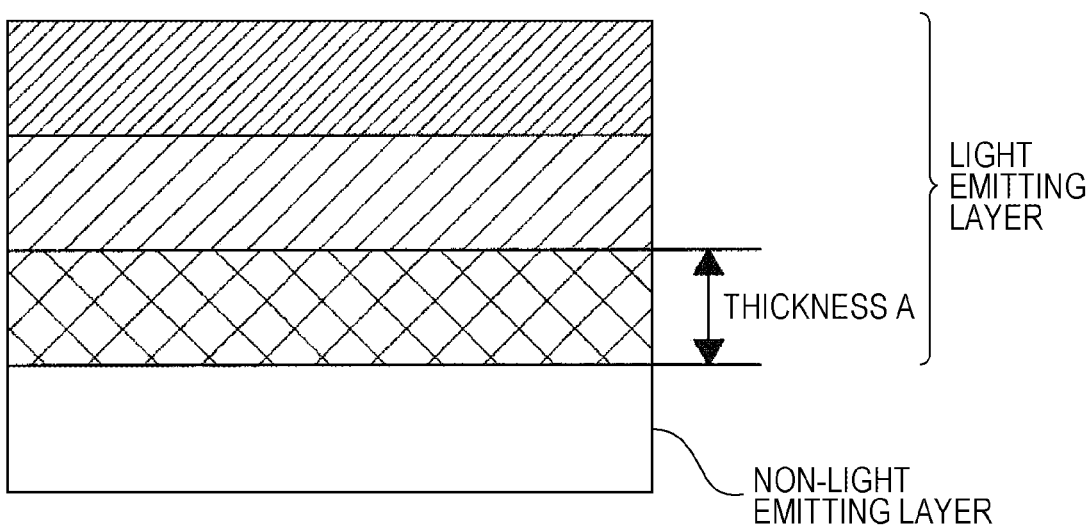
FIG. 2 is a schematic view of a scintillator panel according to one embodiment of the present invention.
Figure 3:
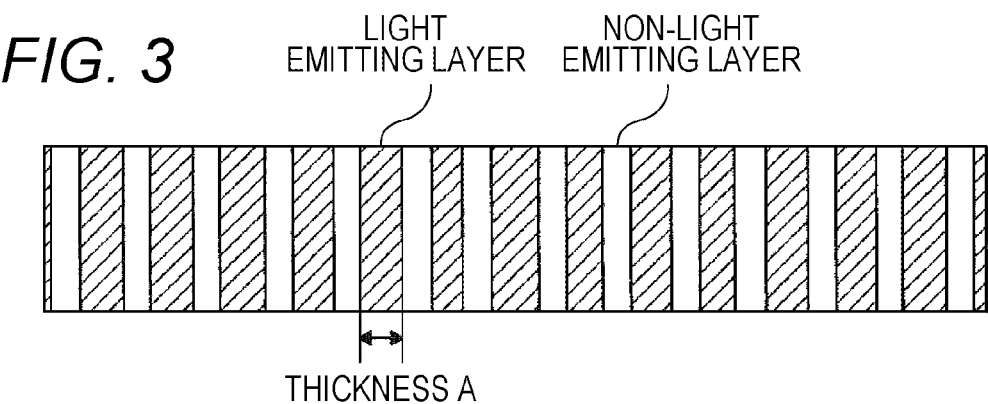
FIG. 3 is a schematic view of a scintillator panel according to one embodiment of the present invention.

The scintillator panel according to an embodiment of the present invention is not particularly limited as long as having the above-described light emitting layer and non-light emitting layer. However, examples of the scintillator panel include an ultrathin film scintillator (first embodiment) formed of a single light emitting layer and a single non-light emitting layer, as illustrated in FIG. 1, a multilayer scintillator (second embodiment) in which a light emitting layer and a non-light emitting layer are disposed in a direction perpendicular to an incident direction of radiation and at least two kinds of light emitting layers are laminated on a surface of the non-light emitting layer, as illustrated in FIG. 2, and a laminated scintillator (third embodiment) having a structure in which a light emitting layer having a function of emitting light by receiving a radiation such as an X-ray and a non-light emitting layer are alternately laminated in a direction substantially parallel to an incident direction of radiation, as illustrated in FIG. 3. Particle diagrams are omitted in FIGS. 2 and 3.

The thickness of a pair of light emitting layer and non-light emitting layer in a direction perpendicular to an incident direction, that is, the thickness thereof in a laminating direction (hereinafter, lamination pitch) is not particularly limited.

In the first and second embodiments, if a flexible non-light emitting layer is used, a radiation image can be acquired in a state in which a scintillator is curved or disposed along the shape of a subject. Alternatively, a scintillator may be attached to a subject to acquire a radiation image. For example, a radiation image may be acquired by attaching a scintillator to the abdomen or chest of a human body and irradiating the scintillator with an X-ray to convert the X-ray that has passed through a subject into an image or by using a positron emission tomography (PET) drug for a PET test. As in Flexible radioluminescence imaging for FDG-guided surgery/Medical Physics 43, 5298 (2016), application to pathology observation/diagnosis is possible by attaching a scintillator to a tissue collected by surgery or the like.

A protective layer may be disposed on a surface of a scintillator in order to prevent scratching and contamination of the surface of the scintillator, for example, during storage or use. The scintillator may be used while the protective layer is disposed, or may be used alter the protective layer is removed.

Various transparent resins can be used for the protective layer. Specifically, the protective layer can be formed by laminating a transparent resin film made of polyethylene terephthalate, polyethylene, polyvinylidene chloride, polyamide, polyimide, or the like on a phosphor layer. Alternatively, the protective layer can be formed by preparing a protective layer coating liquid having a proper viscosity by dissolving a transparent resin such as a cellulose derivative, polyvinyl chloride, polyvinyl acetate, a vinyl chloride-vinyl acetate copolymer, polycarbonate, polyvinyl butyral, polymethyl methacrylate, polyvinyl formal, or polyurethane, applying the protective layer coating liquid onto a scintillator, and drying the protective layer coating liquid.

A member for holding a scintillator may be disposed in order to facilitate handling of the scintillator. For example, the member for holding a scintillator is disposed on a part or the whole of a front surface or a back surface of the scintillator, outside a region of the scintillator surfaces, or the like, and may be separable from the scintillator. The scintillator can be held without directly touching the scintillator surface. Therefore, breakage and contamination of the scintillator surface and damage such as bending can be prevented, and troubles in attachment to a subject can be prevented.

The holding member may be a device generally used for carrying a semiconductor, such as a vacuum suction device or an electrostatic suction device. Alternatively, a sheet that is fixed by pressure-sensitive adhesion or adhesion and can be easily peeled off by a treatment such as heat UV, cooling, or an ultrasonic wave after completion of each process and before packing may be used.

The scintillator may be attached to a subject via a pressure-sensitive adhesive layer or an adsorption layer in order to facilitate attachment to a subject. A non-light emitting layer or a protective layer disposed in the scintillator may function as a pressure-sensitive adhesive layer or an adsorption layer. This makes it possible to prevent deviation and peeling after attachment.

In the second embodiment, the laminated scintillator is formed of three layers of a first light emitting layer, a second light emitting layer, and a third light emitting layer, but two or more light emitting layers are only required. When a radiation is incident on light emitting layers, the light entitling layers generate scintillation light having different emission wavelengths. The scintillation light is incident on a light receiving element array, and the scintillation light that has passed through a color filter layer is incident on a photoelectric conversion element. A member (for example, a substrate or the like) other than a light emitting layer may be disposed between the light emitting layers. In the second embodiment, if the cumulative 50% particle diameter $D_{50}$ and the cumulative 90% particle diameter $D_{90}$ of phosphor particles contained in a light emitting layer adjacent to a non-light emitting layer satisfy the above relational formula, the particle diameters of phosphor particles contained in another light emitting layer are not necessarily limited, but more preferably satisfy a similar relational formula.

The first to third light emitting layers are not particularly limited as long as generating scintillation light having different wavelengths. In order to generate scintillation light having different wavelengths, a material of a base material of the scintillator constituting a light emitting layer may be changed, or the kind and concentration of an emission center added to the base material may be changed.

In the second embodiment, scintillation light generated in light emitting layers can be discriminated and detected. A radiation detector can thereby acquire a detection result of a radiation for each thickness of the scintillator.

In the case of the third embodiment, a ratio between the thickness of a light emitting layer and the thickness of a non-light emitting layer in a laminating direction (hereinafter duty ratio) is derived from Talbot interference conditions. In general, the lamination pitch is preferably 0.5 to 50 µm, and the duty ratio is preferably 30/70 to 70/30. In order to obtain a diagnostic image with a sufficient area, the repeated lamination number in a lamination pitch is preferably 1,000 to 500,000.

Figure 5:
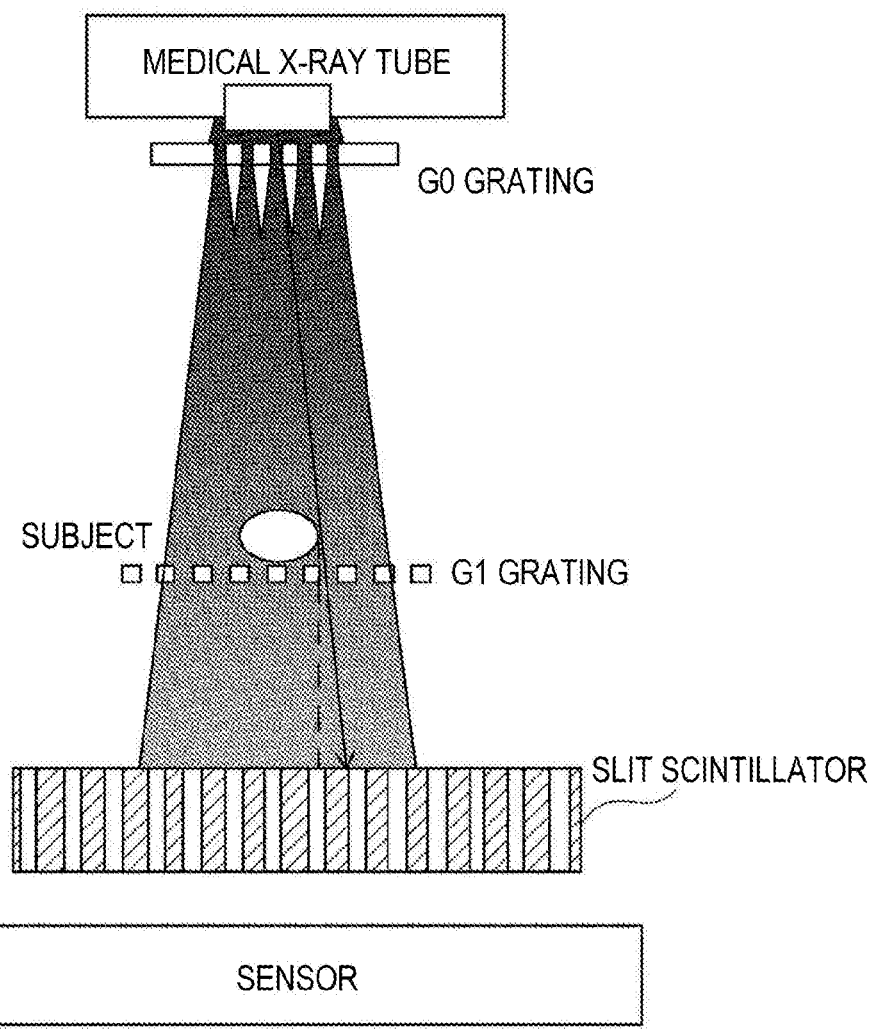
FIG. 5 is a schematic configuration diagram of a Talbot scintillator.

In the third embodiment, light can be transmitted, to a detector through a non-light emitting layer, and therefore brightness and sharpness are not lowered. In addition, this laminated, scintillator panel can also increase the area, and the layer thickness, which has been conventionally difficult, and can arbitrarily adjust a lamination pitch. The scintillator panel illustrated in FIG. 3 can increase the layer thickness, has high brightness and MTF, and also reduces a noise due to X-ray vignetting or the like. Such a scintillator panel can image a phase contrast image. Therefore, the scintillator panel of the third embodiment can be suitably used for a Talbot system. FIG. 5 is a schematic configuration diagram of a Talbot scintillator including the scintillator panel according to an embodiment the present invention.

Next, a Talbot-Lau imaging device sets the scintillator panel to which a photoelectric conversion panel is bonded such that the surface to which the photoelectric conversion panel is bonded becomes an incident surface of an X-ray, and a plurality of moire images each having moire fringes is imaged by a method based on the principle of a fringe scanning method.

Figure 6:
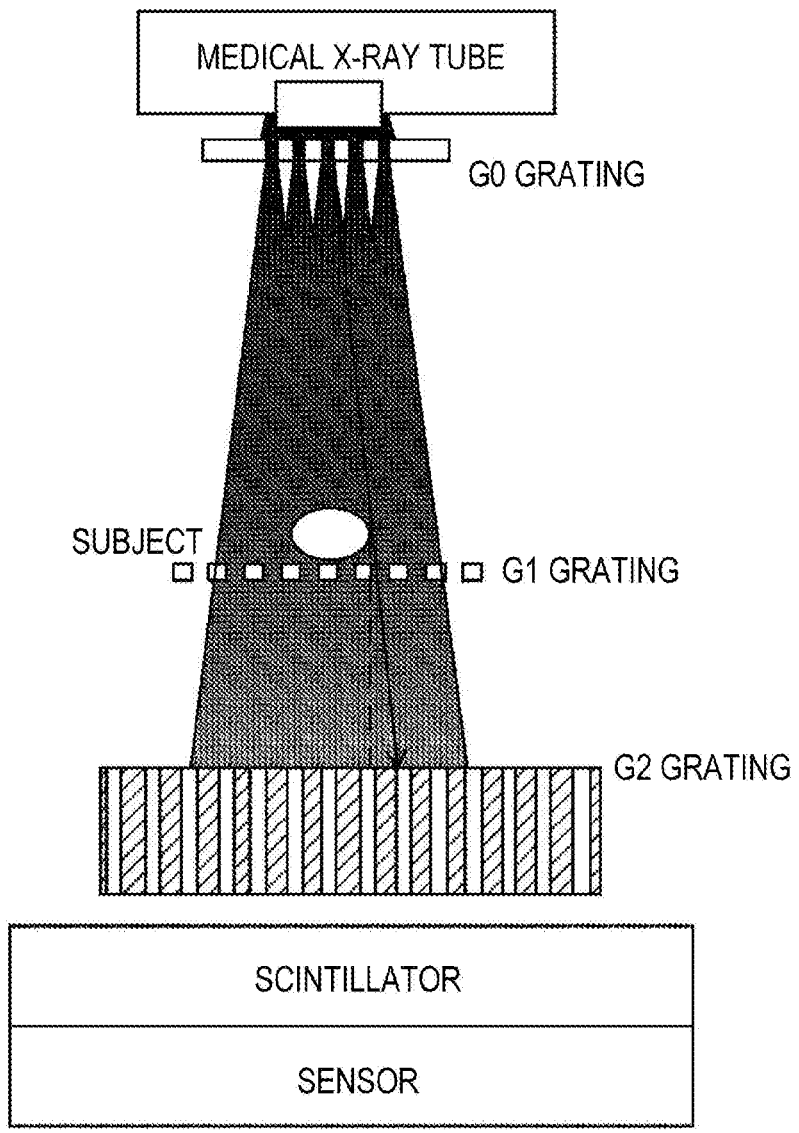
FIG. 6 is a schematic configuration diagram of a Talbot-Lau interferometer.

Note that the Talbot-Lau imaging device described, with reference to FIG. 6 can include an X-ray source, a first grating (that is, a so-called G1 grating), a second grating (that is, a so-called G2 grating), and an X-ray detector known as a flat panel detector (FPD) similarly to an X-ray imaging device using a Talbot interferometer. The Talbot-Lau imaging device further includes a source grating (also referred to as a multi-slit or the like, a so-called G0 grating) disposed near the X-ray source between the X-ray source and the first grating.

In the third embodiment, referencing FIG. 5, the scintillator panel already has a function of the G2 grating, and therefore the scintillator can be used even while the G2 grating is removed from the device. Incidentally, the Talbot imaging device is described in detail in JP 2016-220865 A, JP 2016-220787 A, JP 2016-209017 A, JP 2016-150173 A and the like.

Note that being substantially parallel means being almost parallel. Being perfectly parallel and being parallel with some inclination or curvature are included in a category of substantially parallel. Such a slit-like scintillator can also have a large area. Light emitted by a radiation in the scintillators as described above can be converted into an electric signal via a detector to acquire a digital image.

Light Emitting Layer

The light emitting layer in the present invention is a layer containing a phosphor as a main component, and contains phosphor particles functioning as a scintillator, a binder resin, and a void.

As the scintillator, it is possible to appropriately use a substance which can convert a radiation such as an X-ray into light having a different wavelength such as visible light. Specifically, a scintillator and a phosphor described at pp. 284 to 299 of "Phosphor Handbook" (edited by Phosphor Research Society, Ohmsha, Ltd., 1987) and a substance described in "Scintillation Properties (http://scintillator.l-bl.gov/)" (Web homepage U.S. Lawrence Berkeley National Laboratory) can be considered. However, even a substance not described here can be used as a scintillator as long as the substance "can convert a radiation such as an X-ray into light having a different wavelength such as visible light".

Specific examples of the composition of the scintillator include the following. First, examples of the composition of the scintillator include a metal halide phosphor represented by a basic composition formula (I):

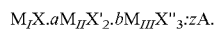

In the above basic composition formula (I), $M_I$ represents an element which can become a monovalent cation, that is, at least one selected from the group consisting of lithium (Li), sodium (Na), potassium (K), rubidium (Rb), cesium (Cs), thallium (Tl), silver (Ag), and the like.

$M_{II}$ represents an element which can become a divalent cation, that is, at least one selected from the group consisting of beryllium (Be), magnesium (Mg), calcium (Ca), strontium (Sr), barium (Ba), nickel (Ni), copper (Cu), zinc (Zn), cadmium (Cd), and the like.

$M_{III}$ represents at least one selected from the group consisting of scandium (Sc), yttrium (Y), aluminum (Al), gallium (Ga), indium (In), and elements belonging to lanthanoid. The lanthanoid refers to elements from atomic symbols 57 to 71, that is, elements from lanthanum (La) to lutetium (Lu) (that is, La, Ce, Pr, Nd, Pm, Sm, Eu, Gd, Tb, Dy, Ho, Er, Tm, Yb, and Lu).

X, X' and X" each represent a halogen element, and may represent different elements or the same element.

A represents at least one element selected from the group consisting of Y, Ce, Pr, Nd, Sm, Eu, Gd, Tb, Dy, Ho, Er, Tm, Yb, Lu, Na, Mg, Cu, Ag (silver), Tl, and Bi (bismuth).

a, b, and z independently represent values within ranges of 0≤a<0.5, 0≤b<0.5, and 0≤z<1.0, respectively.

Examples of the composition of the scintillator include a rare earth activated metal fluorohalide phosphor represented by a basic composition formula (II): $M_{II}FX:zLn$.

In the above basic composition formula (II), $M_{II}$ represents at least one alkaline earth metal element, Ln represents at least one element belonging to lanthanoid, and X represents at least one halogen element. z represents a value within a range of 0<z≤0.2.

Examples of the composition of the scintillator include a rare earth oxysulfide phosphor represented by a basic composition formula (III): $Ln_2O_2S:zA$.

In the above basic composition formula (III), Ln represents at least one element belonging to lanthanoid, and A represents at least one element selected from the group consisting of Y, Ce, Pr, Nd, Sm, Eu, Gd, Tb, Dy, Ho, Er, Tm, Yb, Lu, Na, Mg, Cu, Ag (silver), Tl, and Bi (bismuth). z represents a value within a range of 0<z<1.

Particularly, $Gd_2O_2S$ using gadolinium (Gd) as Ln is preferable because it is known that by using terbium (Tb), dysprosium (Dy), or the like as an element of A, $Gd_2O_2S$ exhibits high luminous characteristics in a wavelength region in which a sensor panel receives light most easily.

Examples of the composition of the scintillator include a metal sulfide phosphor represented by a basic composition formula (IV): $M_{II}S:zA$.

In the above basic composition formula (IV), $M_{II}$ represents an element which can become a divalent cation, that is, at least one element selected from the group consisting of an alkaline earth metal, zinc (Zn), strontium (Sr), gallium (Ga), and the like, and A represents at least one element selected from the group consisting of Y, Ce, Pr, Nd, Sm, Eu, Gd, Tb, Dy, Ho, Er, Tm, Yb, Lu, Na, Mg, Cu, Ag (silver), Tl, and Bi (bismuth). z represents a value within a range of 0<z<1.

Examples of the composition of the scintillator include a metal oxoate phosphor represented by a basic composition formula (V): $M_{IIa}(AG)_b:zA$.

In the above basic composition formula (V), $M_{II}$ represents a metal element which can become a cation, (AG) represents at least one oxo acid group selected from the group consisting of a phosphate, a borate, a silicate, a sulfate, a tungstate, and an aluminate, and A represents at least one element selected from the group consisting of Y, Ce, Pr, Nd, Sm, Eu, Gd, Tb, Dy, Ho, Er, Tm, Yb, Lu, Na, Mg, Cu, Ag (silver), Tl, and Bi (bismuth).

a and b represent any value which can be according to a valence of a metal or an oxo acid group. z represents a value within a range of 0<z<1.

Examples of the composition of the scintillator include a metal oxide phosphor represented by a basic composition formula (VI): $M_aO_b$:zA.

In the basic composition formula (VI), M represents at least one element selected from the metal elements $M_I$ to $M_{III}$ which can be cations, and is particularly preferably a metal belonging to the lanthanoid. Specific examples thereof include $Gd_2O_3$ and $Lu_2O_3$.

A represents at least one element selected from the group consisting of Y, Ce, Pr, Nd, Sm, Eu, Gd, Tb, Dy, Ho, Er, Tm, Yb, Lu, Na, Mg, Cu, Ag (silver), Tl, and Bi (bismuth).

a and b represent any value which can be according to a valence of a metal or an oxo acid group. z represents a value within a range of 0<z<1.

Examples of the composition of the scintillator include a metal acid halide phosphor represented by a basic composition formula (VII): LnOX:zA.

In the above basic composition formula (VII), Ln represents at least one element belonging to lanthanoid, X represents at least one halogen element, and A represents at least one element selected from the group consisting of Y, Ce, Pr, Nd, Sm, Eu, Gd, Tb, Dy, Ho, Er, Tm, Yb, Lu, Na, Mg, Cu, Ag (silver), Tl, and Bi (bismuth). z represents a value within a range of 0<z<1.

Among the above phosphor particles, a rare earth phosphor is preferable, and the rare earth phosphor preferably contains any one of $Gd_2O_2S$, $Lu_2O_2S$, and $Lu_2O_3$ as a main component. As the element A, Tb, Eu, or the like is preferable.

As illustrated in FIG. 2, in a case where light emitting layers having different wavelengths are formed, the emission wavelength of each of the light emitting layers is set according to the material of a base material of the scintillator, the kind of an emission center added, and the concentration of the emission center. For example, in a case of $GdAlO_3$, the emission wavelength varies depending on the kind of the emission center. Specifically, rare earth elements $Tb^{3+}$, $Eu^{3+}$, $Pr^{3+}$, and $Ce^{3+}$ can be used as the emission center. In addition, these emission centers are contained in an amount of 0.001 mol % or more such that a function as a scintillator is effectively exhibited. Using a detection result of each of the light entitling layers by the radiation detector, an image processing means corrects a positional deviation between the detection results of the light emitting layers according to an incident angle of a radiation and then superimposes the detection results on each other.

The light emitting layer contains a binder resin as a binder of phosphor particles. The binder resin is preferably a material transparent to an emission wavelength of the scintillator so as not to inhibit propagation of light emitted from the scintillator.

The binder resin is not particularly limited as long as keeping an object of the present invention, and examples of the binder resin include a natural polymer such as protein (for example, gelatin), a polysaccharide (for example, dextran), or gun arabic; and a synthetic polymer such as polyvinyl butyral, polyvinyl acetate, nitrocellulose, ethylcellulose, a vinylidene chloride-vinyl chloride copolymer, poly (meth)acrylate, a vinyl chloride-vinyl acetate copolymer, polyurethane, cellulose acetate butyrate, polyvinyl alcohol, polyester, an epoxy resin, a polyolefin resin, a polyamide resin, a polyurethane-based resin, an acrylic resin, or a silicone resin. Incidentally, these resins may be crosslinked with a crosslinking agent such as epoxy or isocyanate, and these binder resins may be used singly or in combination of two or more kinds thereof.

The binder resin may be either a thermoplastic resin or a thermosetting resin. Considering a manufacturing process described below, a hot-melt resin is preferably used. For the hot-melt resin, for example, a resin containing a polyolefin-based resin, a polyamide-based resin, a polyester-based resin, a polyurethane-based resin, or an acrylic resin as a main component can be used. Among these resins, a resin containing a polyolefin-based resin as a main component is preferable from viewpoints of light transmittance, moisture resistance, and adhesiveness. Examples of the polyolefin-based resin include an ethylene-vinyl acetate copolymer (EVA), an ethylene-acrylic acid copolymer (EAA), an ethylene-acrylate copolymer (EMA), an ethylene-methacrylic acid copolymer (EMAA), an ethylene-methacrylate copolymer (EMMA), and an ionomer resin. Note that these resins may be used as a so-called polymer blend obtained by combining two or more kinds thereof.

The content of the binder resin in the light emitting layer is preferably 1 to 70 vol %, more preferably 5 to 50 vol %, and still more preferably 10 to 30 vol %. If the content is lower than the lower limit of the above range, sufficient adhesiveness cannot be obtained. Conversely, if the content is higher than the upper limit of the above range, the content of the scintillator is insufficient, and the amount of light emitted decreases.

A void is present inside the light emitting layer or at an interface with the non-light emitting layer. A porosity is not particularly limited, as long as satisfying a predetermined refractive index. Note that the porosity is calculated according to the following formula using a measured volume (area×thickness) of a laminate and a theoretical volume (weight density) of the laminate.

(Measured volume of laminate−theoretical volume of laminate)/theoretical volume of laminate×100

If the area of a laminate is constant, the porosity is calculated according to the following formula using a measured thickness of the laminate and a theoretical thickness (weight/density/area) of the laminate.

(Measured thickness of laminate−theoretical thickness of laminate)/theoretical thickness of laminate×100

The porosity of the light emitting layer is preferably more than 0 and 30 vol % or less. If the porosity exceeds the above range, a filling ratio of the scintillator decreases and the brightness may be lowered.

As a means for forming a void inside the light emitting layer, for example, the light emitting layer may contain bubbles in a process of manufacturing the light emitting layer, or hollow polymer particles may be added to the light emitting, layer. As a means for forming irregularities on a surface of the light emitting layer or the non-light emitting layer, for example, an irregular treatment such as a blast treatment or an emboss treatment may be applied to a surface of the layer. In a case where the light emitting layer is formed by applying a composition containing phosphor particles and a binder resin onto a polymer film, irregularities are formed on a surface of the light emitting layer, and a void can be formed at a contact interface with the polymer film. The sizes of the irregularities can be arbitrarily adjusted by controlling the particle diameters and dispersiveness of phosphor particles.

Non-Light Emitting Layer

The non-light emitting layer in the present invention is a layer that does not emit light itself and does not contain a scintillator as a main component. The content of a scintillator component in the non-light emitting layer is less than 10 vol %, preferably less than 1 vol %, and most preferably 0 vol %.

The non-light emitting layer desirably contains various glasses, a polymer material, a metal, or the like as a main component. These materials may be used singly or in combination of a plurality of kinds thereof. Specific examples of the material include: a plate glass such as quartz, a borosilicate glass, or a chemically reinforced glass; ceramic such as sapphire, silicon nitride, or silicon carbide;

a semiconductor such as silicon, germanium, gallium arsenide, gallium phosphorus, or gallium nitrogen;

a polymer such as a polyester (for example, polyethylene terephthalate (PET) or polyethylene naphthalate (PEN)), an aliphatic polyamide such as nylon, an aromatic polyamide (aramid), polyimide, polyamideimide, polyetherimide, polyethylene, polypropylene, polycarbonate, triacetate, cellulose acetate, epoxy, bismaleimide, polylactic acid, a sulfur-containing polymer such as polyphenylene sulfide or polyethersulfone, polyetheretherketone, a fluorocarbon resin, an acrylic resin, or polyurethane; and a bionanofiber containing a metal foil such as aluminum, iron, or copper, chitosan, cellulose, or the like, such as a carbon fiber or a glass fiber (particularly a fiber reinforced resin sheet containing these fibers).

As the non-light emitting layer, a film-like non-light emitting layer is preferable from a viewpoint of handling during manufacture.

In the present invention, in order to guide light to a light detection sensor or the like through an inside of a non-scintillator, the non-light emitting layer is preferably formed of a transparent material, particularly preferably formed of a transparent resin.

The non-light emitting layer preferably further contains transparent fine particles together with the transparent resin. The transparent fine particles are not particularly limited as long as the non-light emitting layer satisfies a refractive index as described below. However, in general, examples of the transparent fine particles include organic resin particles formed of a thermoplastic resin such as a methyl methacrylate polymer, a methyl methacrylate-methyl acrylate copolymer, a methyl methacrylate-styrene copolymer, or a styrene polymer. Inorganic fine particles such as talc, glass beads, silicone particles, an inorganic oxide, an inorganic nitride, or metal salt particles (for example, a carbonate, a sulfate, or a chloride) can also be used. Incidentally, even if the refractive index of a material itself is high, the refractive index of the whole layer can be adjusted by an average particle diameter. Therefore, a material of the transparent fine particles itself does not need to be transparent.

Examples of the inorganic fine particles include a white pigment such as $TiO_2$ (anatase type or rutile type), MgO, $PbCO_3.Pb(OH)_2$, $BaSO_4$, $Al_2O_3$, M(II)FX (M(II): at least one atom selected from Ba, Sr, and Ca, X: Cl atom or Br atom), $CaCO_3$, ZnO, $Sb_2O_3$, $SiO_2$, $ZrO_2$, lithopone $[BaSO_4.ZnS]$, talc, magnesium silicate, basic silisulfate, basic lead phosphate, or aluminum silicate. Examples of the inorganic fine particles further include glass beads, resin beads, hollow particles having a hollow part therein, multi hollow particles having many hollow parts therein, and porous particles. These particles may be used singly or in combination of two or more kinds thereof.

The blending amount of the transparent resin and the transparent fine particles is adjusted such that the non-light emitting layer has a predetermined refractive index. If the transparent fine particles are contained, adjustment of the refractive index is easy, and light is also refracted/scattered at a particle interface. Therefore, emitted light can efficiently pass through the non-light emitting layer.

Method for Forming Light Emitting Layer

As a method for forming the light emitting layer, a top surface of the non-light emitting layer may be coated with a composition in which the phosphor particles and a binder resin are dissolved or dispersed in a solvent or a composition prepared by heating and melting a mixture containing the phosphor particles and a binder resin.

In a case where a top surface of the non-light emitting layer is coated with a composition in which the phosphor particles and a binder resin are dissolved or dispersed in a solvent, examples of a usable solvent include a lower alcohol such as methanol, ethanol, isopropanol, or n-butanol, a ketone such as acetone, methyl ethyl ketone, methyl isobutyl ketone, or cyclohexanone, an aromatic compound such as toluene, benzene, cyclohexane, cyclohexanone, or xylene; an ester of a lower fatty acid such as methyl acetate, ethyl acetate, or n-butyl acetate and a lower alcohol, an ether such as dioxane, ethylene glycol monoethyl ether, ethylene glycol monomethyl ether, methoxypropanol propylene glycol monomethyl ether, or propylene glycol monomethyl ether acetate, benzenetriol, a halogenated hydrocarbon such as methylene chloride or ethylene chloride, and mixtures thereof. The composition may include various additives such as a dispersant for improving dispersiveness of phosphor particles in the composition, or a curing agent or a plasticizer for improving a bonding force between a binder resin and the phosphor particles in the light emitting layer formed.

Examples of the dispersant used for such an object include phthalic acid, steamic acid, caproic acid, and a lipophilic surfactant.

A coating means with a composition for forming the light emitting layer is not particularly limited, and a usual coating means such as a doctor blade, a roll coater, a knife coater, an extrusion coater, a die coater, a gravure coater, a lip coater, a capillary type coater, or a bar coater can be used.

In a case where the scintillator according to the second or third embodiment of the present invention is formed, the scintillator is formed through a process of laminating a light emitting layer repeatedly, or laminating a light emitting layer and a non-light emitting layer repeatedly and then bonding the light emitting layer and the non-light emitting layer to each other.

A method for repeatedly laminating a light emitting layer and a non-light emitting layer is not particularly limited. A light emitting layer and a non-light emitting layer individually formed may be each divided into a plurality of sheets, and then the sheets may be laminated alternately and repeatedly. In the present invention, preferably, a plurality of partial laminates in which the light emitting layer and the non-light emitting layer are bonded to each other is formed, and then the plurality of partial laminates is laminated to form the laminate because the lamination number and the thickness of the laminate can be easily adjusted.

For example, a partial laminate formed of a pair of light emitting layer and non-light emitting layer may be formed in advance, the partial laminate may be divided into a plurality of sheets, and the sheets may be laminated repeatedly. At this time, it is only required to dispose a desired functional layer separately in any sheet and to perform lamination such that the sheets are disposed at an appropriate interval.

If a partial laminate formed of a light emitting layer and a non-light emitting layer has a film shape that can be wound up, lamination can be efficiently performed by winding the partial laminate around a core. The winding core may be cylindrical or flat. More efficiently, a repeated laminate of light emitting layers and non-light emitting layers, manufactured by the above method, may be joined (integrated) to each other by pressurization, heating, or the like, then may be divided into a plurality of sheets, and the sheets may be repeatedly laminated.

When the partial laminate is laminated, it is only required to dispose a functional layer so as to have a predetermined layer interval.

A method for forming a partial laminate formed of a light emitting layer and a non-light emitting layer is not particularly limited. A polymer film may be selected as a non-light emitting layer, and one surface thereof may be coated with a composition containing phosphor particles and a binder resin to form a light emitting layer. Both surfaces of the polymer film may be coated with a composition containing phosphor particles and a binder resin.

As described above, when the partial laminate is formed by coating a top surface of a film constituting a non-light emitting layer with a composition containing phosphor particles and a binder resin, a process can be simplified, and division into a plurality of sheets is easy. A dividing method is not particularly limited, and an ordinary cutting method is selected.

A transfer substrate coated with a light emitting layer in advance may be transferred onto a film including a non-light emitting layer. The transfer substrate is detached by a means such as peeling as necessary.

In the third embodiment, the light emitting layer and the non-light emitting layer are bonded to each other by pressurizing the laminate such that the light emitting layer and the non-light emitting layer are substantially parallel to an incident direction of radiation.

By heating the repeated laminate of the plurality of light emitting layers and non-light emitting layer in a state pressurized so as to have a desired size, a lamination pitch can be adjusted to a desired value.

A method for pressurizing the repeated laminate of the plurality of light emitting layers and non-light emitting layer so as to have a desired size is not particularly limited. However, the repeated laminate is preferably pressurized while a spacer made of a metal or the like is disposed in advance in order to prevent the laminate from being compressed to a desired size or less. A pressure at this time is preferably 1 MPa to 10 GPa. If the pressure is lower than the lower limit of the above range, it may be impossible to deform a resin component contained in the laminate to a predetermined size. If the pressure is higher than the upper limit of the above range, a spacer may be deformed, and the laminate may be compressed to a desired size or less. By heating the laminate in a pressurized state, bonding can be stronger.

A source emitting a radiation such as an X-ray is generally a point wave source. Therefore, in a case where each of the light emitting layers and non-light emitting layers is formed completely in parallel, in a peripheral region of the laminated scintillator illustrated in FIG. 3, an X-ray is incident obliquely. As a result, in the peripheral region, a phenomenon that a radiation does not sufficiently pass therethrough, so called vignetting occurs. Vignetting becomes a more serious problem as the scintillator has a larger area.

This problem can be solved, in the laminated scintillator panel illustrated in FIG. 3, if a radiation incident side is referred to as a first surface and a side facing the first surface is referred to as a second surface, by making a lamination pitch of the light emitting layer and the non-light emitting layer on the second surface larger than a lamination pitch of the light emitting layer and the non-light emitting layer on the first surface and disposing each of the light emitting layers and non-light emitting layers parallel to an incident direction of radiation. Specifically, this problem can be solved by bending the laminated scintillator panel or forming the laminated scintillator panel into an inclined structure even if the laminated scintillator panel is not bent. In the present invention, by making both the first surface and the second surface of the inclined laminated scintillator panel flat, the scintillator panel can be in close contact with a generally rigid and flat photoelectric conversion panel as well. This scintillator panel is preferable from a viewpoint of improving image quality. Meanwhile, in a case where the laminated scintillator panel is bent, a photoelectric conversion panel also needs to follow the laminated scintillator panel. Therefore, the photoelectric conversion panel is preferably made of a flexible material.

At an interface between the light emitting layer and the non-light emitting layer of the scintillator panel according to an embodiment of the present invention, a functional layer such as a light shielding layer for suppressing diffusion of light emitted from the scintillator may be disposed in order to improve sharpness. The light shielding layer is not particularly limited as long as having a function of suppressing propagation of light emitted from the scintillator, and may have a light reflecting function or a light absorbing function, for example.

In the present invention, a joining end face where a plurality of light emitting layers and non-light emitting layer is joined is preferably flattened. Particularly, by flattening a surface on a radiation incidence side, the opposite side thereto, or both sides thereof, scattering of scintillator light at the joining end face can be suppressed, and sharpness is improved. A flattening method is not particularly limited, and energy such as an ion, a plasma, or an electron beam may be emitted in addition to machining such as cutting, grinding, or polishing. In the case of machining, machining is preferably performed in a direction parallel to a laminated structure so as not to damage the laminated structure of the light emitting layer and the non light emitting layer.

In the scintillator panel in the present invention, a surface on a radiation incidence side, the opposite side thereto, or both sides thereof are preferably bonded to a support to be held as necessary. Note that the non-light emitting layer can also serve as a support in the first and second embodiments.

As the support, various glasses, a polymer material, a metal, and the like that can transmit a radiation such as an X-ray can be used. Examples thereof include a plate glass such as quartz, a borosilicate glass, or a chemically reinforced glass; a ceramic substrate such as sapphire, silicon nitride, or silicon carbide; a semiconductor substrate (photoelectric conversion panel such as silicon, germanium, gallium arsenide, gallium phosphide, or gallium nitride; a polymer film (plastic film) such as a cellulose acetate film, a polyester resin film, a polyethylene terephthalate film, a polyamide film, a polyimide film, a triacetate film, or a polycarbonate film; a metal sheet such as an aluminum sheet, an iron sheet, or a copper sheet; a metal sheet having a cover layer of an oxide of the metal; a carbon fiber-reinforced resin (CFRP) sheet; and an amorphous carbon sheet. The support has a thickness preferably of 50 μm to 2,000 μm, more preferably of 50 to 1,000 μm.

A method for bonding the scintillator panel to the support is not particularly limited. For example, an adhesive, a double-sided tape, or a hot-melt sheet can be used. In a case where the scintillator panel is bonded to the support, the opposite surface to the bonding surface may be flattened.

A layer reflecting or absorbing light emitted from the scintillator may be disposed depending on an intended use between the scintillator panel and the support. By disposing a layer reflecting light emitted from the scintillator, brightness is improved. By disposing a layer absorbing light emitted from the scintillator, sharpness is improved. The support itself may have a function of reflecting or absorbing light emitted from the scintillator.

Photoelectric Conversion Sensor

A scintillator panel according to an embodiment may further include a photoelectric conversion sensor.

The photoelectric conversion sensor absorbs light emitted from the light emitting layer, converts the light into an electric signal by converting the light into a form of a charge, and outputs information included in the emitted light as an electric signal to an outside of a radiation detector. The photoelectric conversion sensor is not particularly limited as long as being able to perform a function thereof, and can be a conventionally known one.

In the photoelectric conversion sensor, a photoelectric conversion element is incorporated in a sensor panel. The configuration of the photoelectric conversion sensor is not particularly limited. However, usually, a substrate for a sensor panel of a photoelectric conversion element, an image signal output layer, and a photoelectric conversion element are laminated in this order.

For example, the photoelectric conversion element may be formed of a transparent electrode, a charge generation layer excited by incident light to generate a charge, and a counter electrode. Any of the transparent electrode, the charge generation layer, and the counter electrode can be conventionally known ones. The photoelectric conversion element may be formed of an appropriate photosensor, and for example, may be formed of a plurality of photodiodes two-dimensionally disposed or a two-dimensional photosensor such as a charge coupled device (CCD) or a complementary metal-oxide-semiconductor (CMOS).

The image signal output layer accumulates a charge obtained by the photoelectric conversion element and outputs a signal based on the accumulated charge. The image signal output layer may have any structure as long as having such a function, and can be formed, for example, using a capacitor as a charge accumulating element that accumulates a charge generated by a photoelectric conversion element for each pixel and a transistor as an image signal output element that outputs an accumulated charge as a signal. Here, a thin film transistor (TFT) is exemplified as a preferable transistor.

In the photoelectric conversion sensor, a plurality of photoelectric conversion elements is disposed on a matrix in the same plane, each of the photoelectric conversion elements (pixels) converts an optical signal into an electric signal, and the electric signal is sequentially output outside an imaging element for each of the pixels.

By causing the scintillator panel to face the photoelectric conversion panel, light emitted from the scintillator by a radiation can be converted into a electric signal, and a digital image can be acquired. The scintillator panel and the photoelectric conversion panel may face each other while being not in a contact with each other. However, in order to reduce optical loss at an interface between the scintillator panel and the photoelectric conversion panel, the scintillator panel and the photoelectric conversion panel are preferably bonded to each other with a transparent material (light transmitting material) having a refractive index of more than 1.0 (air).

Light Transmitting Material Layer

A light transmitting material layer is formed of an organic resin. The light transmitting material layer may have a multilayer structure or may include an air layer, an adhesive functional layer, and the like.

The light transmitting material layer is formed so as to be in close contact with each of a surface of the scintillator and a surface of the photoelectric conversion element sensor.

The thickness of the light transmitting material layer needs to be reduced in order to prevent diffuse of light emitted from the scintillator, and is preferably 50 μm or less, and more preferably 30 μm or less.

A component constituting the light transmitting material layer is not particularly limited as long as an object of the present invention is not impaired, but a thermosetting resin, a hot-melt sheet, or a pressure-sensitive adhesive sheet is preferable.

Examples of the thermosetting resin include a resin containing an acrylic resin, an epoxy-based resin, a silicone-based resin, or the like as a main component. Among the resins, a resin containing an acrylic resin or a silicone-based resin as a main component is preferable from a viewpoint of low temperature thermal curing. Examples of commercially available products thereof include methyl silicone-based JCR 6122 manufactured by Dow Corning Toray Co., Ltd.

The hot-melt sheet in the present invention is a sheet-like adhesive resin (hereinafter referred to as a hot-melt resin) which is solid at room temperature and is made of a nonvolatile thermoplastic material without containing water or a solvent. By inserting a hot-melt sheet between adherends, melting the hot-melt sheet at a temperature equal to or higher than a melting point, and then solidifying the hot-melt sheet at a temperature equal to or lower than the melting point, the adherends can be bonded to each other via the hot-melt sheet. The hot-melt resin does not contain a polar solvent, a solvent, or water. Therefore, the hot-melt resin does not deliquesce a light emitting layer (for example, a phosphor layer having a columnar crystal structure formed of an alkali halide) formed of a deliquescent phosphor even if the hot-melt resin comes into contact with the light emitting layer, and therefore is suitable for bonding the photoelectric conversion element and the light emitting layer to each other. In addition, the hot-melt sheet does not contain a residual volatile matter, and therefore shrinks a little due to drying and also has excellent gap filling property and dimensional stability.

Specific examples of the hot-melt sheet include those based on a resin such as a polyolefin-based resin, a polyamide-based resin, a polyester-based resin, a polyurethane-based resin, an acrylic resin, or an EVA-based resin depending on a main component. Among these sheets, those based on a polyolefin-based resin, an EVA-based resin, or an acrylic resin are preferable from viewpoints of light transmittance and adhesiveness.

The light transmitting material layer may be a pressure-sensitive adhesive sheet. Specific examples of the pressure-sensitive adhesive sheet include those containing an acrylic resin, a urethane-based resin, a rubber-based resin, a silicone-based resin, or the like as a main component. Among these sheets, those containing an acrylic resin or a silicone-based resin as a main component are preferable from viewpoints of light transmittance and adhesiveness.

In a case where the light transmitting material layer is formed of a thermosetting resin, the thermosetting resin is applied onto the light emitting layer or the photoelectric conversion element by a technique such as spin coating, screen printing, a dispenser, or the like.

In a case where the light transmitting material layer is formed of a hot-melt sheet, the light transmitting material layer is formed by inserting the hot-melt sheet between the scintillator panel and the photoelectric conversion element and heating the hot-melt sheet under reduced pressure.

The pressure-sensitive adhesive sheet is bonded by a lamination device or the like.

Furthermore, the light transmitting material layer may be formed of a fiber optic plate (FOP). FOP is an optical device with a bundle of optical fibers of several μm, and can propagate incident light to the photoelectric conversion element at high efficiency and low distortion. In addition, FOP has a high radiation shielding effect, and can prevent radiation damage to various elements constituting a photo-detector used in a radiation image converter.

A commercially available one can be selected for FOP based on a radiation shielding ratio thereof, a visible light transmittance thereof, and the like. FOP is joined to a partitioned scintillator and the photoelectric conversion element panel via a connecting member. As the connecting member, a double-sided pressure-sensitive adhesive sheet, a liquid curing type pressure-sensitive adhesive, an adhesive, or the like is used. An optical pressure-sensitive adhesive sheet or a pressure-sensitive adhesive is particularly preferably used. As the adhesive, either an organic material or an inorganic material may be used. For example, an acrylic material, an epoxy-based material, a silicone-based material, a natural rubber-based material, a silica-based material, a urethane-based material, an ethylene-based material, a polyolefin-based material, a polyester-based material, a polyurethane-based material, a polyamide-based material, a cellulose-based material, and the like are appropriately used. These materials can be used singly or in mixture thereof. In addition, as the structure of the pressure-sensitive adhesive sheet, a sheet in which a pressure-sensitive adhesive layer is formed on both sides of a core material such as PET, a sheet formed as a single-layer pressure-sensitive adhesive layer without a core material, and the like are used.

EXAMPLES

Hereinafter, the present invention will be described with reference to Examples, but the present invention is not limited to such Examples at all.

[Film Thickness]

The film thickness of a light emitting layer was measured using a film thickness meter SP-1100D manufactured by Toyo Corporation.

Example 1-1

Phosphor particles formed of $Gd_2O_2S$:Tb having $D_{50}$ of 2.4 μm and $D_{90}$ of 4.6 μm were mixed with a polyester resin (Vylon 200 manufactured by Toyobo Co., Ltd., Tg=67° C.) in a methyl ethyl ketone (boiling point 79.5° C.) solvent so as to have a volume fraction of 75:25. The resulting mixture was dispersed with a propeller mixer. Methyl ethyl ketone was further added thereto in order to adjust the viscosity to prepare a phosphor coating liquid having a viscosity of 100 CP.

A PET film (thickness: 2.5 μm) was used as a non-light emitting layer. The phosphor coating liquid was applied onto the PET film using a doctor blade, and then dried (drying condition: 80° C. for 20 minutes) to manufacture a laminated scintillator having a light emitting layer having a thickness of 2.5 μm.

Comparative Example 1-1

A laminated scintillator having a light emitting layer having a thickness of 2.5 μm was manufactured in a similar manner to Example 1-1 except that phosphor particles formed of $Gd_2O_2S$:Tb having $D_{50}$ of 2.4 μm and $D_{90}$ of 6.1 μm were used in Example 1-1.

Example 1-2

A laminated scintillator having a light emitting layer having a thickness of 2.5 μm was manufactured in a similar manner to Example 1-1 except that phosphor particles formed of $Lu_2O_3$:(Eu) having $D_{50}$ of 2.4 nm and $D_{90}$ of 3.0 μm were used in Example 1-1.

Example 2-1

A phosphor coating liquid having a viscosity of 100 CP was prepared in a similar manner to Example 1-1 except that phosphor particles formed of $Gd_2O_2S$:Tb having $D_{50}$ of 11.3 μm and $D_{90}$ of 22.1 μm were used as the phosphor particles.

A PET film (thickness: 25 μm) was used as a non-light emitting layer. The phosphor coating liquid was applied onto the PET film using a doctor blade, and then dried (drying condition: 80° C. for 20 minutes) to manufacture a laminated scintillator having a light emitting layer having a thickness of 13 μm.

Comparative Example 2-1

A laminated scintillator having a light emitting layer having a thickness of 13 μm was manufactured in a similar manner to Example 2-1 except that phosphor particles formed of $Gd_2O_2S$:Tb having $D_{50}$ of 12.1 μm and $D_{90}$ of 27.7 μm were used in Example 2-1.

Example 2-2

A laminated scintillator having a light emitting layer having a thickness of 13 μm was manufactured in a similar manner to Example 2-1 except that phosphor particles formed of $Lu_2O_2S$:(Eu) having $D_{50}$ of 12.0 μm and $D_{90}$ of 22.0 μm were used in Example 2-1.

The obtained laminated scintillators were evaluated for MTF as follows.

Each of time scintillators was mounted on a surface of a photoelectric conversion element of PaxScan (FPD:2520 manufactured by Varian Co., Ltd.) in a close contact manner to obtain a radiation image detector, and was evaluated for MTF by an edge method. An X-ray was emitted under a condition of 40 kVp using an X-ray tube, and MTF was calculated from the obtained image data.

Comparative Example 1-1 was judged as "×" for MTF as a standard. If Examples 1-1 and 1-2 each had relatively improved MTF, judgement of "○" was made.

Comparative Example 2-1 was judged as "×" for MTF as a standard. If Examples 2-1 and 2-2 each had relatively improved MTF, judgement of "○" was made.

For a sample judged as × for MTF, a surface condition of a light emitting layer is illustrated in the column of Note. Table 1 illustrates results.

TABLE 1

| | Non-light emitting layer | Light emitting layer | | | | | |
| --- | --- | --- | --- | --- | --- | --- | --- |
| | | Phosphor particles | | | | | |
| | Thickness B | Thickness A | Material | $D_{50}$ particle diameter | $D_{90}$ particle diameter | MTF | Note |
| Comparative Example 1-1 | 2.5 μm | 2.5 μm | $Gd_2O_2S$ | 2.4 μm | 6.1 μm | x | Irregularities on surface of light emitting layer are large |
| Example 1-1 | 2.5 μm | 2.5 μm | $Gd_2O_2S$ | 2.4 μm | 4.6 μm | ○ | |
| Example 1-2 | 2.5 μm | 2.5 μm | $Lu_2O_3$ | 2.4 μm | 3.0 μm | ○ | |
| Comparative Example 2-1 | 25 μm | 13 μm | $Gd_2O_2S$ | 12.1 μm | 27.7 μm | x | Irregularities on surface of light emitting layer are large |
| Example 2-1 | 25 μm | 13 μm | $Gd_2O_2S$ | 11.3 μm | 22.1 μm | ○ | |
| Example 2-2 | 25 μm | 13 μm | $Lu_2O_2S$ | 12.0 μm | 22.0 μm | ○ | |

Example 3-1

Phosphor particles formed of $Gd_2O_2S$:Tb having $D_{50}$ of 2.4 μm and $D_{90}$ of 4.6 μm were mixed with a polyester resin (Vylon 200 manufactured by Toyobo Co., Ltd., Tg=67° C.) in a methyl ethyl ketone (boiling point 79.5° C.) solvent so as to have a volume fraction of 75:25. The resulting mixture was dispersed with a propeller mixer. Methyl ethyl ketone was further added thereto in order to adjust the viscosity to prepare a phosphor coating liquid (A-1) having a viscosity of 100 CP.

A PET film (thickness: 2.5 μm) was used as a non-light emitting layer. The phosphor coating liquid (A-1) was applied onto the PET film using a doctor blade, and then dried (drying condition: 80° C. for 20 minutes) to form a light emitting layer (A-1-1) having a thickness of 2.5 μm.

Next, the phosphor coating liquid (A-1) was applied again onto a surface of the light emitting layer (A-1-1) using a doctor blade, and then dried (drying condition: 80° C. for 20 minutes) to form a light emitting layer (A-1-2) having a thickness of 2.5 μm to manufacture a laminated scintillator.

Example 3-2

Phosphor particles formed of $Lu_2O_3$:Eu having $D_{50}$ of 2.4 μm and $D_{90}$ of 3.0 μm were mixed with a polyester resin (Vylon 200 manufactured by Toyobo Co., Ltd., Tg=67° C.) in a methyl ethyl ketone (boiling point 79.5° C.) solvent so as to have a volume fraction of 75:25. The resulting mixture was dispersed with a propeller mixer. Methyl ethyl ketone was further added thereto in order to adjust the viscosity to prepare a phosphor coating liquid (A-2) having a viscosity of 100 CP.

Next, the phosphor coating liquid (A-2) was applied onto a surface of the light emitting layer (A-1-1) using a doctor blade, and then dried (drying condition: 80° C. for 20 minutes) to form a light emitting layer (A-2-2) having a thickness of 2.5 μm to manufacture a laminated scintillator.

Example 3-3

Phosphor particles formed of $Gd_2O_2S$:Tb having $D_{50}$ of 2.4 μm and $D_{90}$ of 6.1 μm were mixed with a polyester resin (Vylon 200 manufactured by Toyobo Co., Ltd., Tg=67° C.) in a methyl ethyl ketone (boiling point 79.5° C.) solvent so as to have a volume fraction of 75:25. The resulting mixture was dispersed with a propeller mixer. Methyl ethyl ketone was further added thereto in order to adjust the viscosity to prepare a phosphor coating liquid (A-3) having a viscosity of 100 CP.

A PET film (thickness: 2.5 μm) was used as a non-light emitting layer. The phosphor coating liquid (A-2) was applied onto the PET film using a doctor blade, and then dried (drying condition: 80° C. for 20 minutes) to form a light emitting layer (A-2-1) having a thickness of 2.5 μm.

Next, the phosphor coating liquid (A-3) was applied onto a surface of the light emitting layer (A-2-1) using a doctor blade, and then dried (diving condition: 80° C. for 20 minutes) to form a light emitting layer (A-3-2) having a thickness of 2.5 μm to manufacture a laminated scintillator.

Comparative Example 3-1

A PET film (thickness: 2.5 μm) was used as a non-light emitting layer. The phosphor coating liquid (A-3) was applied onto the PET film using, a doctor blade, and then dried (drying condition: 80° C. for 20 minutes) to form a light emitting layer (A-3-1) having, a thickness of 2.5 μm.

Next, the phosphor coating liquid (A-3) was applied again onto a surface of the light emitting layer (A-3-1) using a doctor blade, and then dried (drying condition: 80° C. for 20 minutes) to form a light emitting layer (A-3-2) having a thickness of 2.5 μm to manufacture a laminated scintillator.

Comparative Example 3-2

The phosphor coating liquid (A-2) was applied onto a surface of the light emitting layer (A-3-1) using a doctor blade, and then dried (drying condition: 80° C. for 20 minutes) to form a light emitting layer (A-2-2) having a thickness of 2.5 μm to manufacture a laminated scintillator.

The obtained laminated scintillators were evaluated for MTF. Table 2 illustrates results.

Comparative Example 3-1 was judged as "x" for MTF as a standard. If Example 3-1 had relatively improved MTF, judgement of "○" was made.

Comparative Example 3-2 was judged as "x" for MTF as a standard. If Examples 3-2 and 3-3 each had relatively improved MTF, judgement of "○" was made.

TABLE 2

| | Non-light emitting layer Thickness B | Light emitting layer (1) Thickness A1 | Phosphor particles Material | $D_{50}$ particle diameter | $D_{90}$ particle diameter | Light emitting layer (2) Thickness A2 | Phosphor particles Material | $D_{50}$ particle diameter | $D_{90}$ particle diameter | MTF | Note |
|---|---|---|---|---|---|---|---|---|---|---|---|
| Comparative Example 3-1 | 2.5 μm | 2.5 μm | $Gd_2O_2S$ | 2.4 μm | 6.1 μm | 2.5 μm | $Gd_2O_2S$ | 2.4 μm | 6.1 μm | x | Lamination interface was largely distorted |
| Comparative Example 3-2 | 2.5 μm | 2.5 μm | $Gd_2O_2S$ | 2.4 μm | 6.1 μm | 2.5 μm | $Lu_2O_3$ | 2.4 μm | 3.0 μm | x | Lamination interface was largely distorted |
| Example 3-1 | 2.5 μm | 2.5 μm | $Gd_2O_2S$ | 2.4 μm | 4.6 μm | 2.5 μm | $Gd_2O_2S$ | 2.4 μm | 4.6 μm | ○ | |
| Example 3-2 | 2.5 μm | 2.5 μm | $Gd_2O_2S$ | 2.4 μm | 4.6 μm | 2.5 μm | $Lu_2O_3$ | 2.4 μm | 3.0 μm | ○ | |
| Example 3-3 | 2.5 μm | 2.5 μm | $Lu_2O_3$ | 2.4 μm | 3.0 μm | 2.5 μm | $Gd_2O_2S$ | 2.4 μm | 6.1 μm | ○ | |

Example 4-1

<Method for Manufacturing Plate>

Phosphor particles formed of $Gd_2O_2S$:Tb having $D_{50}$ of 2.4 μm and $D_{90}$ of 4.6 μm were mixed with an ethylene-vinyl acetate-based hot-melt resin (Evaflex EV150 manufactured by Mitsui-du Pont Polychemical, melting point=61° C.) so as to have a solid content ratio (volume fraction) of 50/50 to obtain a composition for forming a light emitting layer. This composition was melted at 200° C., and a top surface of a PET film (non-light emitting layer) having a theoretical film thickness of 2.5 μm (calculated from the weight) was coated with the composition using a die coater so as to have a theoretical film thickness of 2.5 μm (calculated from the weight) to manufacture a partial laminate formed of a non-light emitting layer and a light emitting layer. Thereafter, 20,000 pieces obtained by cutting the partial laminate into pieces of 120 mm×3 mm were laminated.

Subsequently, the laminate was pressurized in parallel to a lamination surface under a pressure of 0.2 GPa using a metallic jig such that the film thickness of the laminate was 120 mm. Furthermore, the laminate was heated in this state at 100° C. for one hour to manufacture a laminated block (120 mm×120 mm×3 mm) formed of the 20,000-layer partial laminate.

One side (surface of 120 mm×120 mm) of the laminated block was flattened by lathe machining, and then an epoxy adhesive was applied thereto, and the side was bonded to a CFRP plate having a thickness of 0.5 mm as a support. Thereafter, the laminated block was cut by lathe machining until the thickness of the laminated block became 0.2 mm, and a laminated scintillator panel (120 mm×120 mm×0.2 mm) was thereby obtained.

<Evaluation Method>

A surface of the laminated scintillator panel on which the CFRP plate was not bonded was bonded to a photoelectric conversion panel (detector) with an optical double-sided tape (CS9861US manufactured by Nitto Denko Corporation), and the resulting product was disposed with respect to an X-ray tube such that an X-ray was incident on the scintillator panel from the surface. At this time, adjustment was performed such that an X-ray was vertically incident on a center position of the 120 mm×120 mm plane of the scintillator panel, and an X-ray irradiation range was set so as to include the entire surface of the scintillator panel. A distance L1 from the X-ray tube to the surface of the scintillator panel was 1.5 m.

With this disposition, a distance a1 from the position of the scintillator panel on which an X-ray was vertically incident from an X-ray irradiation device to an end portion of the scintillator panel was 60 mm, a thickness L2 of the scintillator panel in a radiation incident direction was 0.3 mm, and a total thickness a2 of a light emitting layer and a non-light emitting layer of the scintillator panel was 6 μm.

Under such a positional relationship, an X-ray was emitted under a condition of a tube voltage of 40 kV to obtain an X-ray image. During the irradiation with an X-ray, the disposition of a battery or a circuit board disposed on an X-ray irradiation side of the photoelectric conversion panel inside the device was adjusted so as not to obstruct X-ray transmission. At this time, a signal can be compensated by image correction without changing the disposition inside the device.

Brightness and MTF were measured from the X-ray image acquired in this way. Note that an edge method was used for MTF.

Example 4-2

A laminated scintillator panel was obtained in a similar manner to Example 4-1 except that phosphor particles formed of $Lu_2O_3$ having $D_{50}$ of 2.4 μm and $D_{90}$ of 3.0 μm were used. The positional relationship with the X-ray tube was also similar to that in Example 1.

Comparative Example 4-1

A laminated scintillator panel was obtained in a similar manner to Example 4-1 except that phosphor particles formed of $Gd_2O_2S$:Tb having $D_{50}$ of 2.4 μm and $D_{90}$ of 6.1 μm were used. The positional relationship with the X-ray tube was also similar to that in Example 1.

Comparative Example 4-1 was judged as "x" for MTF as a standard. If Examples 4-1 and 4-2 each had relatively improved MTF, judgement of "○" was made.

Table 3 illustrates results.

TABLE 3

| | Non-light emitting layer Thickness | Light emitting layer | | Scintillator particles | | | | |
|---|---|---|---|---|---|---|---|---|
| | | Thickness | Material | $D_{50}$ particle diameter | $D_{90}$ particle diameter | Other configuration | MTF | Note |
| | B | A1 | | | | | | |
| Comparative Example 4-1 | 2.5 μm | 2.5 μm | $Gd_2O_2S$ | 2.4 μm | 6.1 μm | 20,000 layers of non-light emitting layers and light emitting layer are repeatedly laminated. X-ray is emitted perpendicularly to laminating direction | x | Lamination interface was largely distorted |
| Example 4-1 | 2.5 μm | 2.5 μm | $Gd_2O_2S$ | 2.4 μm | 4.6 μm | 20,000 layers of non-light emitting layers and light emitting layer are repeatedly laminated. X-ray is emitted perpendicularly to laminating direction | o | |
| Example 4-2 | 2.5 μm | 2.5 μm | $Lu_2O_3$ | 2.4 μm | 3.0 μm | 20,000 layers of non-light emitting layers and light emitting layer are repeatedly laminated. X-ray is emitted perpendicularly to laminating direction | o | |

According to an embodiment of the present invention, a light emitting layer contains phosphor particles having an appropriate particle diameter distribution. Therefore, irregularities on a surface of the light emitting layer are reduced, and emitted light is less likely to be scattered on the surface. This improves MTF indicating sharpness of an image.

Such an ultrathin film-like scintillator in which a light emitting layer is formed on paper or a thin film can acquire a radiation image in a state of being curved or bent, and in addition, can acquire a radiation image in a state of being attached along the shape of a subject. It is possible to perform imaging while a distance between a subject and a scintillator is short, and an image with high sharpness can be obtained. In addition, by acquiring a radiation image by attaching an ultrathin film-like scintillator to a lesion tissue collected by surgery or the like and irradiating the lesion tissue with an X-ray or by using a positron emission tomography (PET) drug for a PET test or the like, use for pathological observation and pathological diagnosis is also possible. Therefore, according to an embodiment of the present invention, it is possible to perform rapid pathological diagnosis easily with less invasion.

In addition, in a case of laminating a plurality of light emitting layers, irregularities on a laminated surface are reduced, and emitted light is hardly scattered. A multilayer scintillator having high sharpness can be thereby obtained. If an emission color is changed for each light emitting layer, a higher energy X-ray reaches a deeper part of a scintillator layer. Therefore, the emission color can be changed by a difference in X-ray energy, and it is possible to obtain a radiation image expressing a difference in X-ray energy with a color. It is possible to construct an energy discrimination image even with one shot although the energy discrimination image is conventionally constructed with two shots by changing a tube voltage.

In a case of a laminated scintillator panel in which a light emitting layer and a non-light emitting layer are repeatedly laminated, it is possible to provide a scintillator panel having high brightness and MTF. Such a scintillator panel according to an embodiment of the present invention can be suitably used for a Talbot system. In this case, a scintillator itself has a function of a G2 grating, and therefore the G2 grating is unnecessary. This makes it possible to perform imaging at a higher tube voltage and also to image a thick subject such as a thoracoabdominal part, a thigh part, an elbow joint, a knee joint, or a hip joint.

Conventionally, in image diagnosis for cartilage, MRI is mainly used, and there are disadvantages that imaging cost is high because of use of large-scale equipment and imaging time is long. Meanwhile, according to an embodiment of the present invention, it is possible to image a soft tissue such as cartilage, muscle tendon, or ligament and a visceral tissue with a faster X-ray image at lower cost. Therefore, wide application to, for example, image diagnosis for an orthopedic disease such as rheumatoid arthritis or gonarthrosis, breast cancer, and a soft tissue can be expected.

Although the above embodiments of the present invention have been described and illustrated in detail, the disclosed embodiments are made for purposes of illustration and example only and not limitation. Needless to say, the purpose, state, use, function, and other specifications can be modified appropriately, and the present invention can be implemented according to another embodiment. The scope of the present invention should be interpreted by terms of the appended claims.

What is claimed is:

1. A scintillator panel comprising at least one light emitting layer and at least one non-light emitting layer laminated, wherein the light emitting layer contains phosphor particles, and with a thickness of the light emitting layer represented by A, a relationship among a cumulative 50% particle diameter $D_{50}$ of the phosphor particles based on volume average, a cumulative 90% particle diameter $D_{90}$ of the phosphor particles based on volume average, and the thickness A satisfies, $D_{50}<A$ and $A<D_{90}<2A$, wherein $D_{50}$ and $D_{90}$ are calculated starting at the smallest particle diameter until 50% and 90%, respectively, of the particles are included.

2. The scintillator panel according to claim 1, wherein a relationship between Dso and the thickness A satisfies $0.01<(D_{50}/A)<1$.

3. The scintillator panel according to claim 1, wherein the thickness A of the light emitting layer is 30 μm or less.

4. The scintillator panel according to claim 1, wherein the thickness of the non-light emitting layer is 30 μm or less.

5. The scintillator panel according to claim 1, wherein the light emitting layer and the non-light emitting layer are disposed and laminated in a direction parallel to an incident direction of radiation.

6. The scintillator panel according to claim 1, wherein the light emitting layer and the non-light emitting layer are disposed in a direction perpendicular to an incident direction of radiation, and at least two kinds of light emitting layers are laminated on a surface of the non-light emitting layer.

7. The scintillator panel according to claim 6, wherein a phase contrast image is imaged.

8. A Talbot-Lau imaging device comprising an X-ray source that emits an X-ray and the scintillator panel according to claim 7.

9. The scintillator panel according to claim 1, wherein the phosphor particles are formed of a rare earth phosphor.

10. The scintillator panel according to claim 9, wherein the rare earth phosphor contains any one of $Gd_2O_2S$, $Lu_2O_2S$, and $Lu_2O_3$ as a main component.

* * * * *